United States Patent
Bercier et al.

(10) Patent No.: US 12,385,833 B2
(45) Date of Patent: Aug. 12, 2025

(54) SPECTROSCOPIC EVALUATION OF UNSAPONIFIABLE MATTER IN TALLOW

(71) Applicant: Cargill, Incorporated, Wayzata, MN (US)

(72) Inventors: Martine Cécile Bercier, London (CA); Amanda Louise Carroll, Otsego, MN (US); Tina M. Hoetmer, Valley Center, KS (US); Lyndakaye EmaLee Prior, Princeton, MN (US)

(73) Assignee: Cargill, Incorporated, Wayzata, MN (US)

( * ) Notice: Subject to any disclaimer, the term of this patent is extended or adjusted under 35 U.S.C. 154(b) by 53 days.

(21) Appl. No.: 18/040,404

(22) PCT Filed: Jul. 30, 2021

(86) PCT No.: PCT/US2021/043862
§ 371 (c)(1),
(2) Date: Feb. 2, 2023

(87) PCT Pub. No.: WO2022/031532
PCT Pub. Date: Feb. 10, 2022

(65) Prior Publication Data
US 2023/0296507 A1 Sep. 21, 2023

Related U.S. Application Data

(60) Provisional application No. 63/060,782, filed on Aug. 4, 2020.

(51) Int. Cl.
*G01N 21/359* (2014.01)
*G01N 1/28* (2006.01)
(Continued)

(52) U.S. Cl.
CPC ........... *G01N 21/359* (2013.01); *G01N 1/286* (2013.01); *G01N 33/03* (2013.01); *G01N 33/28* (2013.01); *G01N 2201/0221* (2013.01)

(58) Field of Classification Search
CPC .. G01N 1/286; G01N 21/3577; G01N 21/359; G01N 21/84; G01N 33/03;
(Continued)

(56) References Cited

U.S. PATENT DOCUMENTS

| 5,648,413 A | 7/1997 | Sato |
| 7,194,369 B2 * | 3/2007 | Lundstedt ........ G01N 35/00871 702/104 |

(Continued)

FOREIGN PATENT DOCUMENTS

| CN | 104990889 A | 10/2015 |
| CN | 105203489 A | 12/2015 |

(Continued)

OTHER PUBLICATIONS

Adewale et al., "Determination of the iodine value and the free fatty acid content of waste animal fat blends using FT-NIR." Vibrational Spectroscopy 72 (2014): 72-78.

(Continued)

*Primary Examiner* — Michael P LaPage

(57) ABSTRACT

A characteristic of tallow may be evaluated using a spectrometer (110). For example, optical reflectance data may be obtained from tallow, the reflectance data corresponding to a specified range of infra-red wavelengths. A value corresponding to the characteristic may be output based on the reflectance data generated by the spectrometer (110). The characteristic may include unsaponifiable matter as a percentage or concentration in a sample, for example.

10 Claims, 6 Drawing Sheets

(51) Int. Cl.
*G01N 33/03* (2006.01)
*G01N 33/28* (2006.01)

(58) Field of Classification Search
CPC ... G01N 2021/1761; G01N 2201/0221; G01N 2201/129; G01N 33/18; G01N 33/28
See application file for complete search history.

(56) References Cited

U.S. PATENT DOCUMENTS

| | | | | |
|---|---|---|---|---|
| 8,010,309 | B2* | 8/2011 | Lundstedt | G01N 35/00871 702/104 |
| 11,162,932 | B2* | 11/2021 | Dong | A47J 37/1266 |
| 11,579,132 | B2* | 2/2023 | Dong | G01N 21/3577 |
| 2001/0037182 | A1 | 11/2001 | Hall | |
| 2003/0154044 | A1* | 8/2003 | Lundstedt | G01N 35/00871 702/181 |
| 2006/0063912 | A1 | 3/2006 | Mullane et al. | |
| 2006/0213554 | A1 | 9/2006 | Welch | |
| 2007/0143037 | A1* | 6/2007 | Lundstedt | G01N 21/274 702/30 |
| 2010/0197535 | A1 | 8/2010 | Brossaud | |
| 2011/0054864 | A1 | 3/2011 | Lundstedt | |
| 2011/0293544 | A1 | 12/2011 | Brown | |
| 2012/0232300 | A1* | 9/2012 | Summers | C07C 67/293 422/187 |
| 2013/0008341 | A1 | 1/2013 | Hunt | |
| 2014/0349406 | A1 | 11/2014 | Higgins | |
| 2017/0009181 | A1 | 1/2017 | Kotoneva | |
| 2019/0162658 | A1* | 5/2019 | Zhang | G01N 21/3577 |
| 2021/0270730 | A1* | 9/2021 | Dong | G01N 21/3577 |
| 2023/0168234 | A1* | 6/2023 | Dong | A47J 37/1266 250/341.8 |
| 2023/0273124 | A1* | 8/2023 | Bercier | G01N 33/03 250/341.1 |
| 2023/0273125 | A1* | 8/2023 | Bercier | G01N 21/3577 250/341.1 |

FOREIGN PATENT DOCUMENTS

| | | |
|---|---|---|
| CN | 204945036 U | 1/2016 |
| CN | 207163906 U | 3/2018 |
| CN | 110426368 A | 11/2019 |
| CN | 110726688 A | 1/2020 |
| CN | 211043124 U | 7/2020 |
| DE | 19644722 A1 | 4/1998 |
| EP | 0034047 A1 | 8/1981 |
| JP | 57142546 A | 9/1982 |
| JP | 2018077202 A | 5/2018 |

OTHER PUBLICATIONS

Adomako, "Fatty acid composition and characteristics of Pentadesma butyracea fat extracted from Ghana seeds." Journal of the Science of Food and Agriculture 28.4 (1977): 384-386.

Armenta et al., "The use of near-infrared spectrometry in the olive oil industry." Critical Reviews in Food Science and Nutrition 50.6 (2010): 567-582.

Bellorini et al. "Discriminating animal fats and their origins: assessing the potentials of Fourier transform infrared spectroscopy, gas chromatography, immunoassay and polymerase chain reaction techniques." Analytical and Bioanalytical Chemistry 382 (2005): 1073-1083.

Roodenko et al., "Non-dispersive infrared (NDIR) sensor for real-time nitrate monitoring in wastewater treatment." Optical Fibers and Sensors for Medical Diagnostics and Treatment Applications XIX. vol. 10872. SPIE, 2019. 7 pages.

Shenk et al., "Populations structuring of near infrared spectra and modified partial least squares regression." Crop Science 31.6 (1991): 1548-1555.

Chen, A new approach to near-infrared spectral data analysis using independent component analysis, Jul. 23, 2001, Journal of Chemical Information and Computer Sciences, 992-1001, 41(4).

Galvez-Sola et al., Effectiveness of Near Infrared Reflectance Spectroscopy in the Quick Evaluation of Nitrogen Content in Sewage Sludge, Jan. 1, 2009, Communications in Soil Science and Plant Analysis, vol. 40: 726-735. (Year: 2009).

Maxwell et al., "A rapid, quantitative procedure for measuring the unsaponifiable matter from animal, marine, and plant oils" Journal of the American Oil Chemists' Society 56(6):634-636, Jun. 1979.

Prieto et al.,, A review of the principles and applications of near-infrared spectroscopy to characterize meat, fat, and meat products, Jul. 1, 2017, Applied Spectroscopy, 71(7), 1403-1426.

Schwartz, "Improved method for quantitating and obtaining the unsaponifiable matter of fats and oils" Journal of the American Oil Chemists Society 65(2):246-251, Feb. 1988.

Su et al.,, Development of near infrared reflectance spectroscopy to predict chemical composition with a wide range of variability in beef, Oct. 1, 2014, Meat Science, 110-114, 98(2).

Suehara et al., Rapid and simple determination of oil and urea concentrations and solids content to monitor biodegradation conditions of wastewater discharged from a biodiesel fuel production plant, 2007, J. Near Infrared Spectrosc. vol. 15, pp. 89-96. (Year: 2007).

Tøgersen et al., On-line prediction of chemical composition of semi-frozen ground beef by non-invasive NIR spectroscopy, Apr. 1, 2003, Meat Science, 515-523, 63(4).

* cited by examiner

SPECTROSCOPIC EVALUATION OF UNSAPONIFIABLE MATTER IN TALLOW

CROSS-REFERENCE TO RELATED APPLICATIONS

This application is a national phase application of PCT Application No. PCT/US2021/043862, filed Jul. 30, 2021, which claims the benefit of U.S. Provisional Patent Application No. 63/060,782, filed Aug. 4, 2020, each of which is incorporated herein by reference in its entirety.

BACKGROUND

Scientists employ a variety of analytical tools to assist in quantitative evaluation of various characteristics of products, from raw materials to finished goods. Generally, analytical tools may rely upon careful control and preparation of a sample for evaluation, such as according to a standardized test or evaluation protocol in a "bench" setting. In this manner, traceable and repeatable results may be obtained. Such techniques may be applied to tallow. Use of analytical techniques to evaluate tallow helps to verify or maintain quality throughout the production and distribution process. For example, after processing, bench analytical techniques may be used to verify that minor components are at or below specified levels. Analytical techniques may also be used to assess tallow for a presence of contaminants or adulterants.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The systems and methods described herein use spectroscopy to characterize edible or inedible tallow, such as using a reflectance spectroscopy technique in a near-infrared range of wavelengths. These systems and methods may include evaluating a sample to determine a percentage or concentration of a particular characteristic. For example, the characteristic may include unsaponifiable matter. A value as a percentage or concentration may be output based on raw spectroscopy data output from a spectrometer.

A sample of tallow may be evaluated using the systems and methods described herein. The sample may be taken from a tallow, for example from a tanker, hopper, transport container, etc., such as in-situ on a train car, at a farm, at a distribution or processing facility, or the like. The tallow may be edible or inedible. The sample may be prepared, for example by melting, stirring, shaking, covering, placed in a clear container, such as a petri dish, or cooled (e.g., allowed to solidify), or a slurry cup (e.g., with a specified thickness). For example, a tallow sample may be melted with limited heat and shaken and poured into a petri dish to fill the petri dish (e.g., around 6 g of tallow). A lid may be placed on the petri dish and the tallow may be allowed to solidify (e.g., cool). The prepared samples may be placed into a spectrometer.

The spectrometer may scan the prepared sample, for example with infrared spectroscopy. A processor (e.g., of a spectrometer device) may be used to determine a value corresponding to a characteristic for the prepared sample based on a result of the scan (e.g., based on raw data output by the spectrometer). The value corresponding to the characteristic may be output, for example displayed on a display device of the spectrometer, sent to a remote device (e.g., a mobile device such as a phone for display), or the like. The process may be repeated (e.g., two to four times) with the same prepared sample to generate a value indicative of a central tendency, such as an average or median value. This may help avoid inconsistencies.

Figure 1:
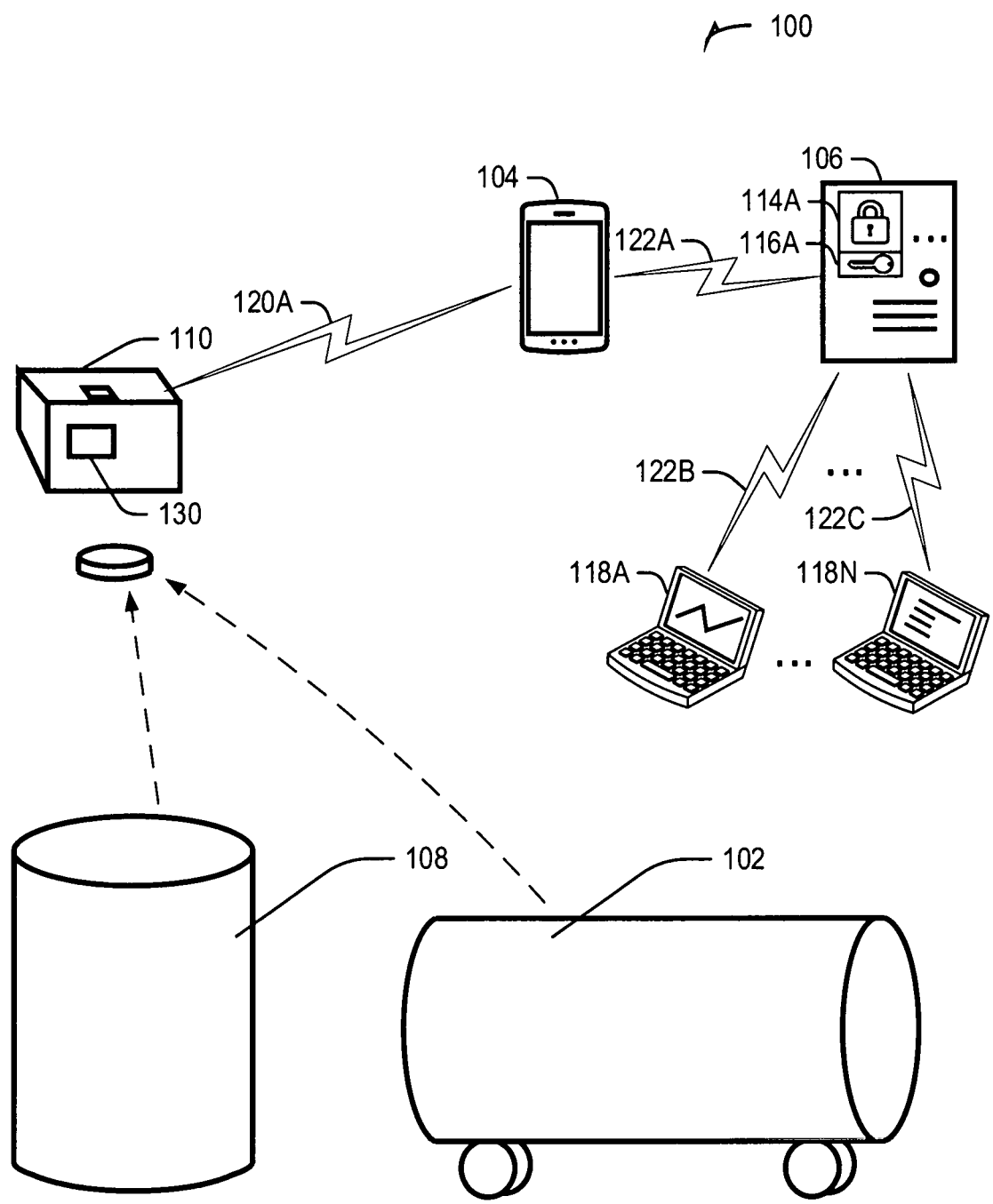
FIG. 1 illustrates generally an example showing a system that may include a spectrometer, such as for characterization of tallow.

FIG. 1 illustrates generally an example showing a system 100 that may include a spectrometer 110, such as for characterization of tallow, such as from a tank 108 or a tanker 102. Evaluation of a characteristic of the tallow may be performed with the tallow within a holding vessel in an example. In another example, the characteristic may be evaluated without needing to remove a sample from the tank 108 or tanker 102. The spectrometer 110 may include a user interface 130, such as including a user input or a display, as mentioned in relation to other examples described herein. In an example, the spectrometer 110 may be portable, such as sized and shaped to be manipulated by a user by hand. The spectrometer may be configured to emit light comprising a specified range of infra-red wavelengths, and to receive a reflection from tallow. The spectrometer 110 may then establish reflectance data corresponding to the received reflection without requiring physical contact between the spectrometer 110 and the tallow.

The spectrometer 110 may include a processor circuit configured to provide reflectance data comprising a series of values corresponding to discrete wavelength values spanning a specified range of wavelengths. As an illustrative example, the specified range may include wavelengths from about 400 nanometers to about 2500 nanometers. The spectrometer 110 may include a housing and hardware configuration similar to the FOSS NIR 5000/6500 or DS2500 (available from Foss, Hilleroed, Denmark) or the SCiO apparatus (available from Consumer Physics, Tel Aviv, Israel). Reflectance data from a range of 750 nanometers to 1070 nanometers may be provided. The use of reflectance spectroscopy in the near-infrared range of wavelengths is illustrative, and other spectroscopic techniques may be used. The spectrometer 110 may be coupled via a wired or wireless communication channel 120A to another device, such as a device 104 (e.g., a mobile device such as a cellular handset, a tablet device, a "phablet" device having a cellular or wireless networking adaptor, a laptop or desktop computer, or a base-station located in a facility housing the frying apparatus 102, as illustrative examples).

The wireless communication channel 120A may be established according to a wireless communication standard such as Bluetooth® (e.g., Bluetooth® Low Energy (BLE) as described in the Bluetooth Core Specification, v. 5.0, published Dec. 6, 2016, by the Bluetooth® Special Interest Group, Kirkland, Washington) or according to one or more other standards (e.g., the Institute of Electrical and Electronics Engineers (IEEE) 802.11 family of standards known as Wi-Fi®, mobile communications standards such as relating to 4G/Long Term Evolution (LTE), or the IEEE 802.15.4 family of standards, as illustrative examples).

The device 104 may include one or more processor circuits coupled to one or more memory circuits. For example, the device 104 may be configured to transform received reflectance data provided by the spectrometer 110 such as using a model profile to generate a value of a characteristic being assessed. The device 104 may be coupled through another wireless communication channel 122A to a repository 106 such as a remotely-located server or a cloud-based (e.g., distributed) facility. For example, the wireless communication channel 122A may be established according to a wireless networking protocol mentioned above, or a digital cellular networking protocol, as illustrative examples. One or more criteria may be applied to the transformed reflectance data. For example, a value of a characteristic being assessed, such as a parameter relating to unsaponifiable matter, may be determined from spectroscopy data for the tallow. The result may be presented to a user. The representation (which may include a color code, such as green or red corresponding to a threshold) may be presented to the user via the user interface 130 of the spectrometer or the device 104, or the like.

In another example, the device 104 serves as an intermediary device, and the repository 106 (or other facility such as a cloud-based resource) may perform the transformation of the reflectance data to establish a value of the characteristic being assessed. In yet another example, the spectrometer 110 includes one or more processor circuits coupled to one or more memory circuits, and the device 104 need not be used. For example, the spectrometer 110 may transmit reflectance data to the repository 106 for processing (e.g., transformation), or the spectrometer 110 may transform reflectance data.

Data generated by the spectrometer may be used to generate a percentage or concentration of a characteristic in a sample. Calibration models, for each product type and analyte as described herein, may be based on an array of data created from the NIR spectra points and the wet chemistry analysis values.

The NIR spectra, including the signature of the samples, is correlated to the reference analysis values for specific analytes, for example a wet chemistry analysis method. This creates an algorithm or calibration model that may be used to predict the analyte values for similar products that fall within the parameter of the calibration model. The NIR spectra points may be generally collected at every 0.5 nm, from 400 to 2500 nm wavelength range, in an example.

To create the algorithm models, the step between points may be widened and only part of the wavelength range may be used. In an example, the math treatments selected are: 1st or 2nd derivatives, Gap of 4 to 24, 1st smoothing 4 to 24, 2nd smoothing 1 or 2

Scatter correction pre-processing may be done using standard normal variate and detrending. An algorithm may be created, for example using a Modified Partial Least Square (MPLS) method, for example based on a process initially defined by Shenk, J. S. and Westerhaus, M. O. (1991), Population Structuring of Near Infrared Spectra and Modified Partial Least Squares Regression. Crop Sciences 31, pp. 1548-1555.

MPLS involves a process of removing multivariate outliers & 'inliers' in a 2-step process. It involves the computation of Mahalanobis distances and in the 1st step data within the 3.0 boundary is selected and in a 2nd step, the data points further than 0.6 from each other are selected. The calibration models may then be developed using dedicated software (e.g., WinISI from Foss Analytics of Denmark).

Similar results may be obtained different software & mathematics, such as with calibrator software or from the many machine learning algorithms or modelling framework available such as MATLAB, Unscrambler, R Earth, Python Py-Earth, Multivariate adaptive regression spline (MARS), or the like.

Figure 2:
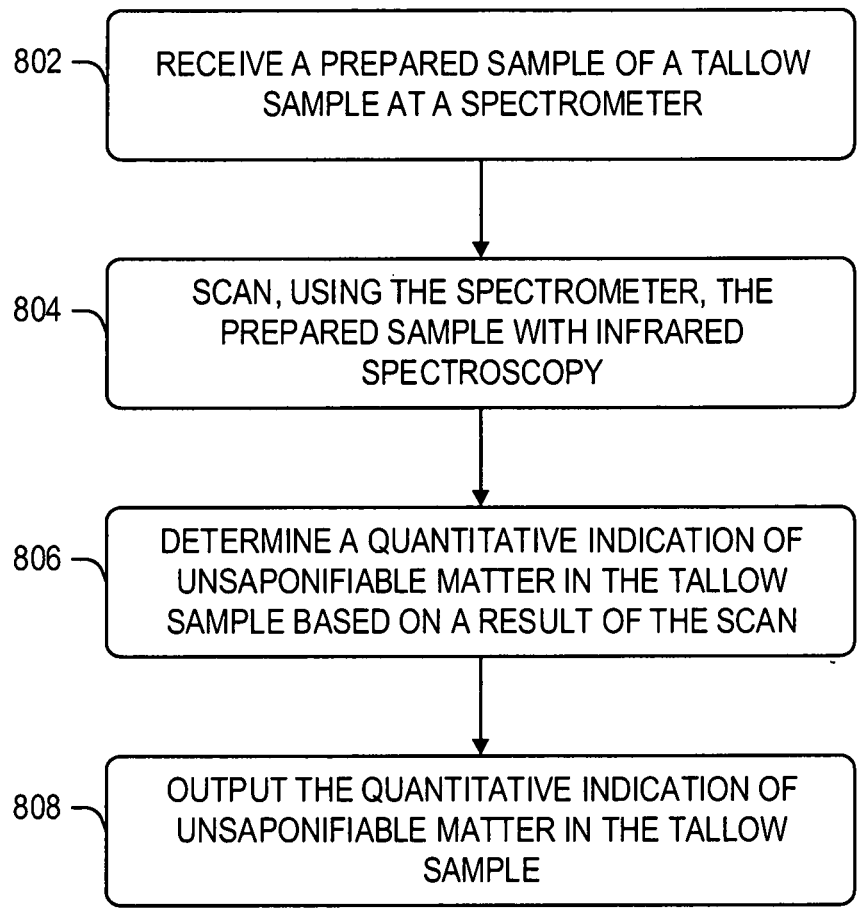
FIG. 2 illustrates generally an example comprising a technique, such as an automated method, for determining an indication of unsaponifiable matter in a tallow sample using a spectrometer.

FIG. 2 illustrates generally an example comprising a technique 800, such as an automated method, for determining an indication of unsaponifiable matter in a tallow sample using a spectrometer. In this example technique 800, the tallow sample may be edible or inedible. The technique 800 includes an operation 802 to receive a prepared sample of a tallow sample at a spectrometer. The sample may be prepared by melting, agitating, or covering the tallow, for example in a petri dish or a slurry cup (e.g., with a specified thickness). The sample may be prepared directly from a mobile tanker or a bulk tanker in an example. The technique 800 may be performed on-site where the sample is extracted.

The technique 800 includes an operation 804 to scan, using the spectrometer, the prepared sample with infrared spectroscopy. The infrared spectroscopy may include infrared transmission spectroscopy or infrared reflection spectroscopy. A wavelength of the infrared spectroscopy may be within a near infrared spectrum, for example (e.g., 780 nm to 2500 nm). In an example, the wavelength may be within a range of frequencies between 400 nanometers and 2500 nanometers. The spectrometer may be a portable or mobile spectrometer.

The technique 800 includes an operation 806 to determine, for example using a processor (e.g., of the spectrometer), an indication of unsaponifiable matter in the tallow sample based on a result of the scan. The indication may include a quantitative indication, such as a relative indication, a ratio, a fraction such as a decimal fraction, or a percentage. Operation 806 may include converting raw spectrometer readings or data to a characteristic value using a formula.

The technique 800 includes an operation 808 to output the indication of unsaponifiable matter in the tallow sample. Operation 808 may include displaying the indication of unsaponifiable matter in the tallow sample on a display of the spectrometer or sending the indication of unsaponifiable matter in the tallow sample to a mobile device for display. In an example, operation 808 may include outputting an average or median of two or more iterations of the technique 800.

Figure 3:
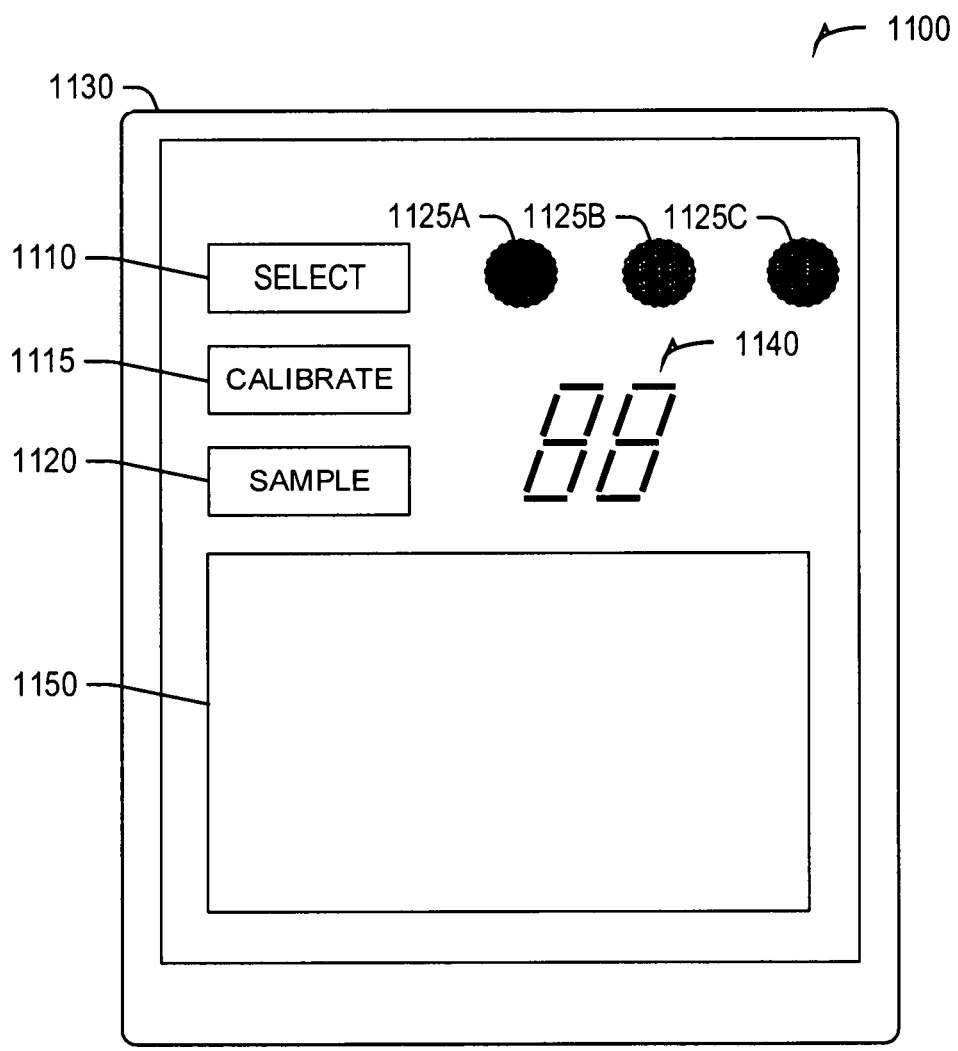
FIG. 3 illustrates generally an example comprising a user input and display, such as a touch-screen user interface, such as may be used to receive inputs to control a spectrometer or to present results, such as a representation of a characteristic of tallow being assessed using the spectrometer.

FIG. 3 illustrates generally an example 1100 comprising a user input and display, such as a touch-screen user interface 1130, such as may be used to receive inputs to control a spectrometer or to present results, such as a representation of a characteristic of tallow being assessed using the spectrometer (such as the spectrometer 110 shown in FIG. 1), or a separate device in communication with the spectrometer, such as a mobile device or tablet. As an illustrative example, an input 1110 may be used to receive an indication from the user that a particular characteristic is to be tested. Another input 1115 may be used to receive an indication from the user that the spectrometer is to be calibrated. An input 1120 may used to receive an indication from the user that a scan of a sample is to be initiated.

As mentioned in relation to various examples herein, data obtained using the spectrometer may be used to output a value of a characteristic being assessed, such as unsaponifiable matter. The value itself may be presented on a display 1150 of the touch-screen user interface 1130 or a simplified representation may be presented (e.g., a pass/fail indication via a light or lights, for example based on a threshold). For example, the simplified representation may include a visual indication that the sample (i.e., tallow) has a value for the characteristic over or below a threshold or within a range, such as via a "traffic light" (green/yellow/red, for example below a first threshold green, within a range between thresholds yellow, and above a second threshold red) style representation having three indicators 1125A, 1125B, or 1125C representing the threshold or range. Such states may be defined in a variety of manners, such as including a first state corresponding to "OK," a second state such as "possibly unusable" or "try again," or a third state indicative that the tallow sample has a characteristic above a threshold for example "not ok."

The interface of the example 1100 of FIG. 3 shows user inputs unified with a display for presentation of results, but these elements may also be separate. For example, the inputs may be provided by soft-keys aligned with a display, or by a separate keypad or input (e.g., switches, knobs, etc.). The display may include a bit-field display or other display (e.g., an LED or liquid-crystal display having pre-defined display elements, such as a numerical indicator 1140 having seven-segment digits or other arrangement or indicators 1125A, 1125B, 1125C comprising LED lamps). As an illustrative example, a unitless scale may be shown, such as a simplified numerical scale having values from one to five, or one to ten, such as having higher values to indicate relative concentration or percentage of the characteristic in the sample. Various aspects may be presented on the display 150, which may include a touchscreen display for receiving user input and displaying information.

Experimentally-Obtained Results

Figure 4:
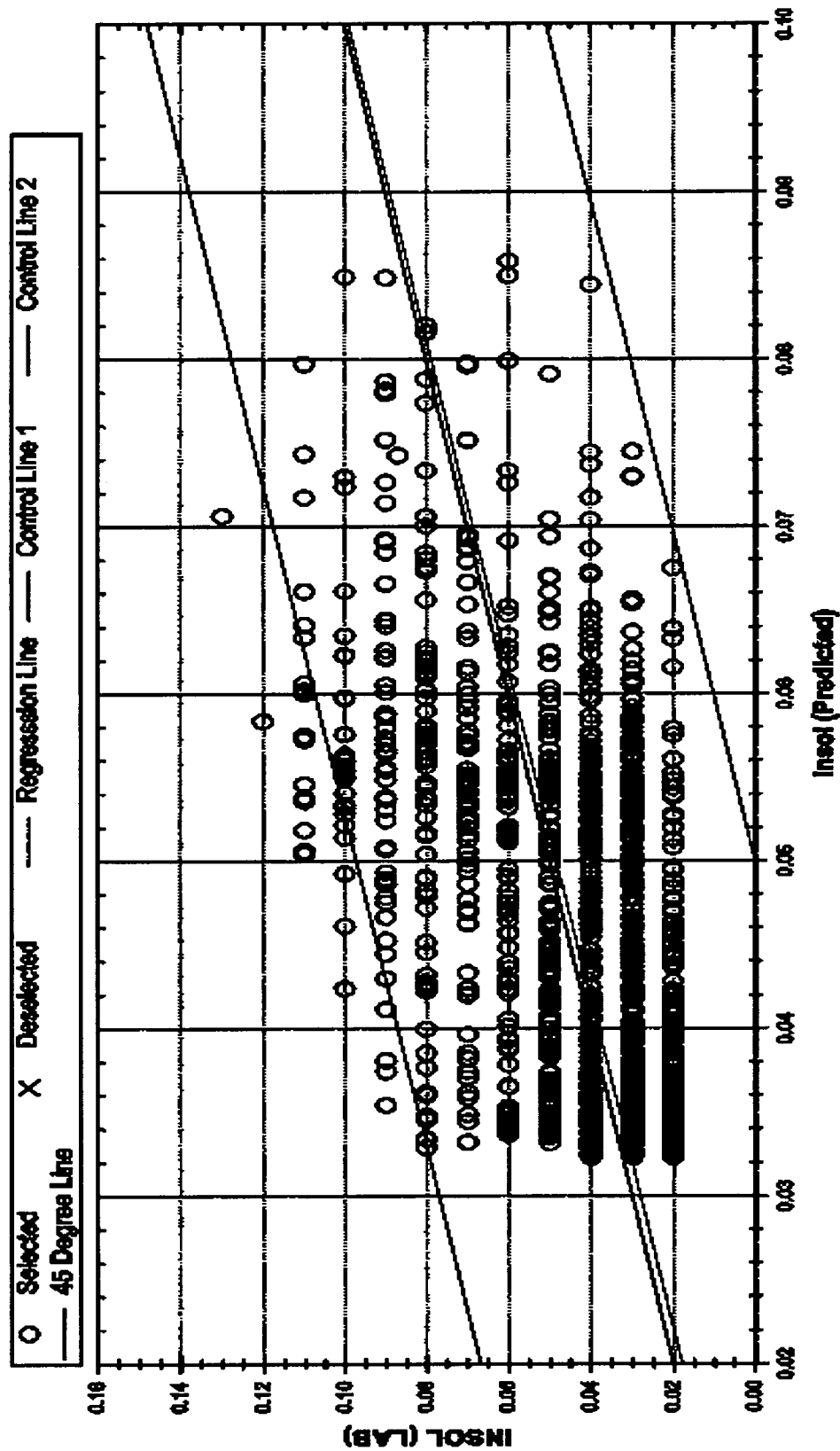
FIGS. 4-5 illustrate generally illustrative examples of experimentally-obtained results including a predicted unsaponifiable matter value obtained by transforming spectroscopic data, plotted versus corresponding measurements of the unsaponifiable matter value using a laboratory technique.
Figure 5:
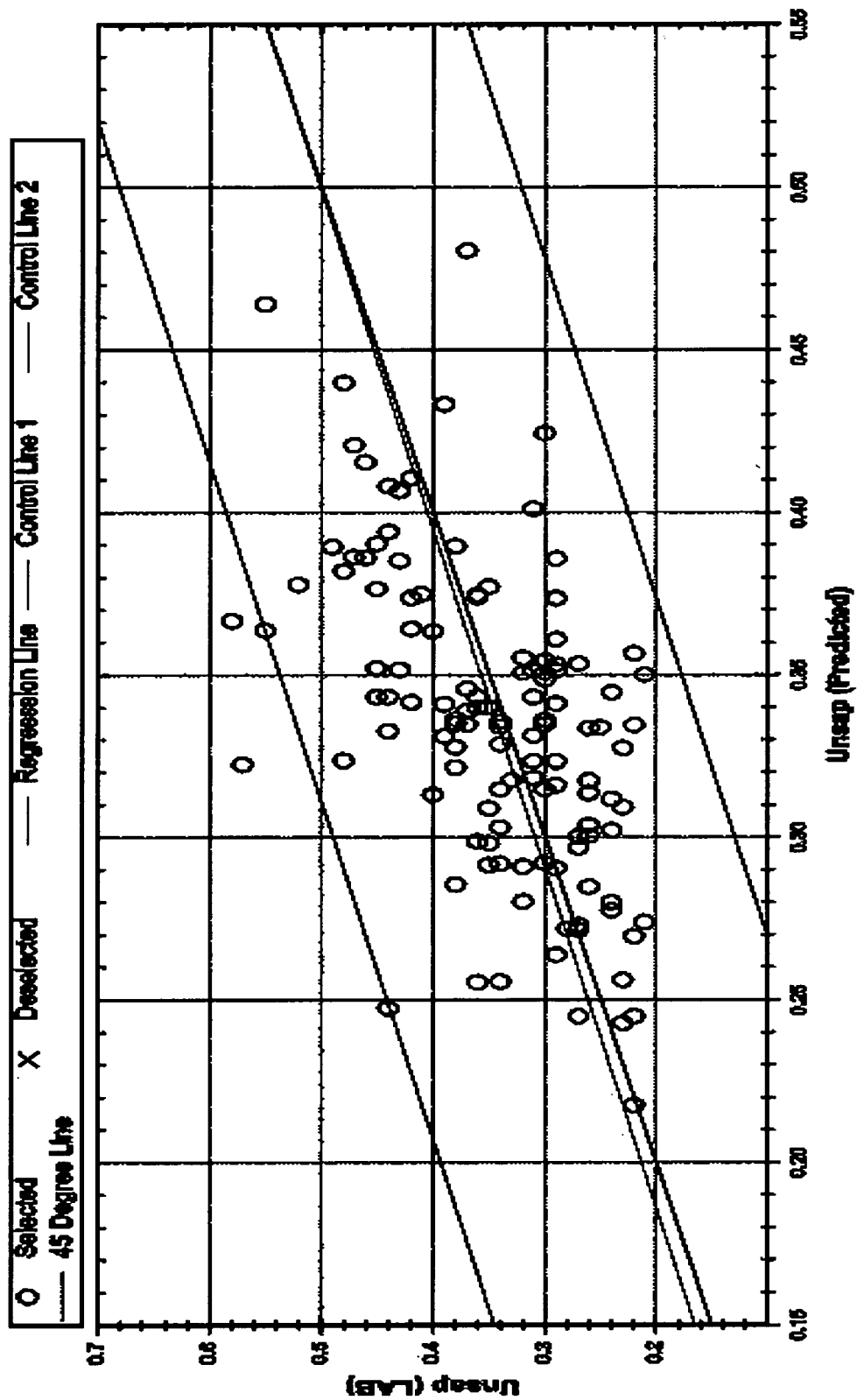

The results shown in FIG. 4 and FIG. 5 were obtained using a DS2500 device with a prepared sample inserted within, as described herein. In each of FIG. 4 and FIG. 5, the results in the graph show a predicted value (from a near-infrared spectroscopy result) against a wet chemistry (e.g., laboratory) derived value for a particular sample. A regression line is shown, which fits within two control lines (e.g., threshold lines of tolerance). A 45-degree line is shown for reference as well (e.g., a perfect fit). The majority of predicted results fit within the control lines, and the regression line fits within the control lines. In an example, the regression line may be determined using a Residual Prediction Deviation (RPD), by taking a standard deviation of characteristic values divided by a Root Mean Square Error or Prediction (RMSEP) value.

FIGS. 4-5 illustrate generally illustrative examples of experimentally-obtained results including a predicted unsaponifiable matter value obtained by transforming spectroscopic data, plotted versus corresponding measurements of the unsaponifiable matter value using a laboratory technique. FIG. 4 illustrates a graph of data obtained using an edible tallow sample and FIG. 5 illustrates a graph of data obtained using an inedible tallow sample. Because the predicted results and laboratory results follow a similar trend line and are expected to be the same regardless of whether the tallow is edible or inedible, a single test may be used for both edible and inedible tallow when testing for unsaponifiable matter.

Figure 6:
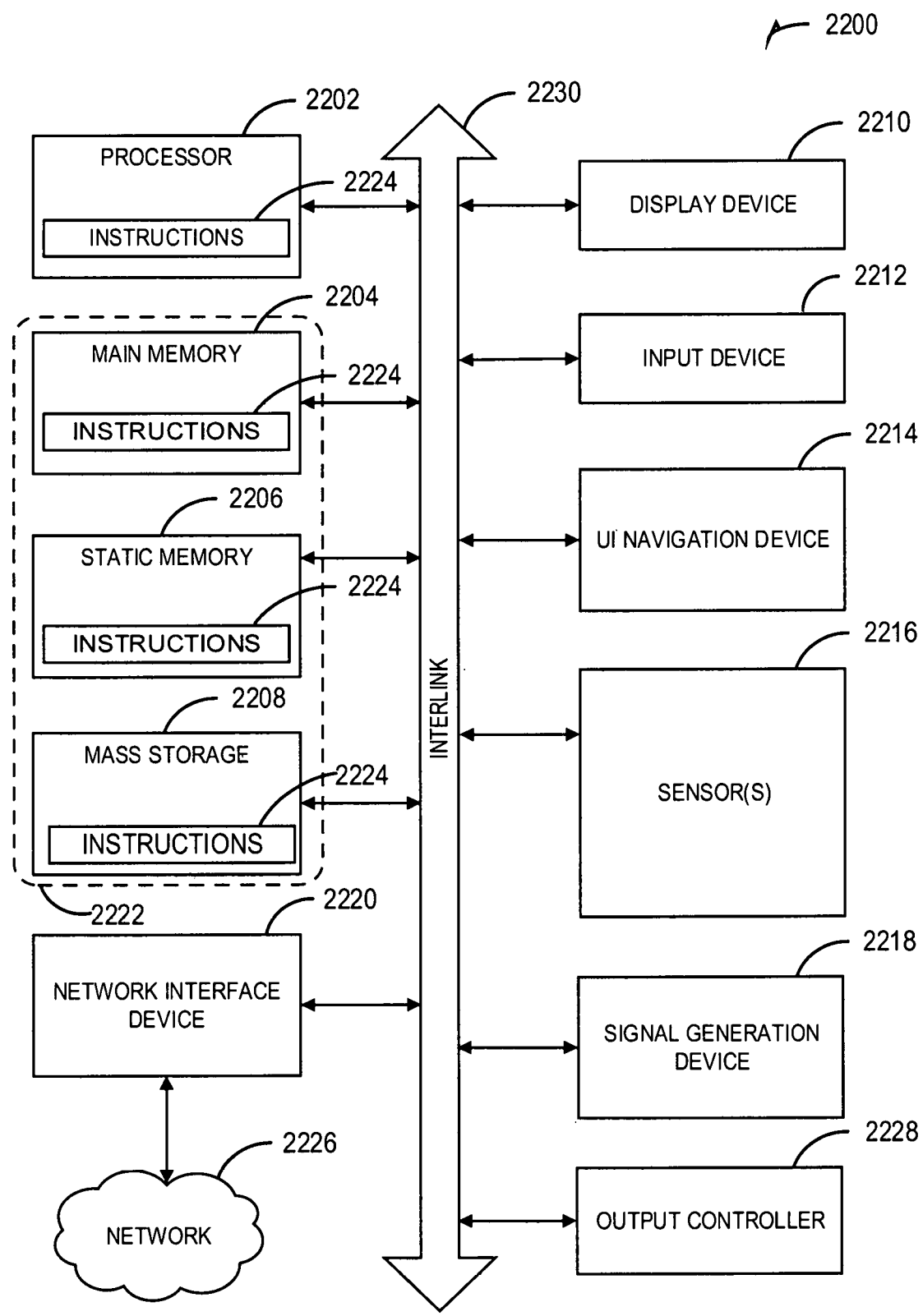
FIG. 6 illustrates a block diagram of an example comprising a machine upon which any one or more of the techniques (e.g., methodologies) discussed herein may be performed.

FIG. 6 illustrates a block diagram of an example comprising a machine 2200 upon which any one or more of the techniques (e.g., methodologies) discussed herein may be performed. The machine 2200 may be included as a portion of elements shown in the system 100 of FIG. 1. In various examples, the machine 2200 may operate as a standalone device or may be connected (e.g., networked) to other machines. In a networked deployment, the machine 2200 may operate in the capacity of a server machine, a client machine, or both in server-client network environments. In an example, the machine 2200 may act as a peer machine in peer-to-peer (P2P) (or other distributed) network environment. The machine 2200 may be a personal computer (PC), a tablet device, a personal digital assistant (PDA), a mobile telephone, a web appliance, a network router, switch or bridge, a portable (e.g., hand-held) spectrometer such as including a microprocessor or microcontroller, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. "Circuitry" refers generally a collection of circuits implemented in tangible entities that include hardware (e.g., simple circuits, gates, logic elements, etc.). Circuitry membership may be flexible over time and underlying hardware variability. Circuitries include members that may, alone or in combination, perform specified operations when operating. In an example, hardware of the circuitry may be immutably designed to carry out a specific operation (e.g., hardwired). In an example, the hardware comprising the circuitry may include variably connected physical components (e.g., execution units, transistors, simple circuits, etc.) including a computer readable medium physically modified (e.g., magnetically, electrically, such as via a change in physical state or transformation of another physical characteristic, etc.) to encode instructions of the specific operation.

In connecting the physical components, the underlying electrical properties of a hardware constituent may be changed, for example, from an insulating characteristic to a conductive characteristic or vice versa. The instructions enable embedded hardware (e.g., the execution units or a loading mechanism) to create members of the circuitry in hardware via the variable connections to carry out portions of the specific operation when in operation. Accordingly, the computer readable medium is communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time.

Machine (e.g., computer system) 2200 may include a hardware processor 2202 (e.g., a central processing unit (CPU), a graphics processing unit (GPU), a hardware processor core, or any combination thereof), a main memory 2204 and a static memory 2206, some or all of which may communicate with each other via an interlink (e.g., bus) 2208. The machine 2200 may further include a display unit 2210, an alphanumeric input device 2212 (e.g., a keyboard), and a user interface (UI) navigation device 2214 (e.g., a mouse). In an example, the display unit 2210, input device 2212 and UI navigation device 2214 may be a touch screen display. The machine 2200 may additionally include a storage device (e.g., drive unit) 2216, a signal generation device 2218 (e.g., a speaker), a network interface device 2220, and one or more sensors 2221, such as a global positioning system (GPS) sensor, compass, accelerometer, or other sensor. The machine 2200 may include an output controller 2228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 2216 may include a machine readable medium 2222 on which is stored one or more sets of data structures or instructions 2224 (e.g., software) embodying or utilized by any one or more of the techniques or functions described herein. The instructions 2224 may also reside, completely or at least partially, within the main memory 2204, within static memory 2206, or within the hardware processor 2202 during execution thereof by the machine 2200. In an example, one or any combination of the hardware processor 2202, the main memory 2204, the static memory 2206, or the storage device 2216 may constitute machine readable media.

While the machine readable medium 2222 is illustrated as a single medium, the term "machine readable medium" may include a single medium or multiple media (e.g., a centralized or distributed database, and/or associated caches and servers) configured to store the one or more instructions 2224.

The term "machine readable medium" may include any medium that is capable of storing, encoding, or carrying instructions for execution by the machine 2200 and that cause the machine 2200 to perform any one or more of the techniques of the present disclosure, or that is capable of storing, encoding or carrying data structures used by or associated with such instructions. Non-limiting machine readable medium examples may include solid-state memories, and optical and magnetic media. Accordingly, machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic or other phase-change or state-change memory circuits; magnetic disks, such as internal hard disks and removable disks; magneto-optical disks; and CD-ROM and DVD-ROM disks.

The instructions 2224 may further be transmitted or received over a communications network 2226 using a transmission medium via the network interface device 2220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks such as conforming to one or more standards such as a 4G standard or Long Term Evolution (LTE)), Plain Old Telephone (POTS) networks, and wireless data networks (e.g., Institute of Electrical and Electronics Engineers (IEEE) 802.11 family of standards known as Wi-Fi®, IEEE 802.15.4 family of standards, peer-to-peer (P2P) networks, among others. In an example, the network interface device 2220 may include one or more physical jacks (e.g., Ethernet, coaxial, or phone jacks) or one or more antennas to connect to the communications network 2226. In an example, the network interface device 2220 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 2200, and includes digital or analog communications signals or other intangible medium to facilitate communication of such software.

Each of the non-limiting examples below can stand on its own, or can be combined in various permutations or combinations with one or more of the other aspects or other subject matter described in this document.

Example 1 is a method for near infrared evaluation of a characteristic of a sample, the method comprising: receiving a prepared sample of the sample at a spectrometer; scanning, using the spectrometer, the prepared sample with infrared spectroscopy; determining, using a processor, a value corresponding to the characteristic for the sample based on a result of the scan; and outputting the value.

In Example 2, the subject matter of Example 1 includes, wherein the prepared sample is prepared by covering the sample in a petri dish or a slurry cup.

In Example 3, the subject matter of Examples 1-2 includes, wherein the infrared spectroscopy includes infrared transmission spectroscopy or infrared reflection spectroscopy.

In Example 4, the subject matter of Examples 1-3 includes, wherein a wavelength of the infrared spectroscopy is within a near infrared spectrum.

In Example 5, the subject matter of Examples 1-4 includes, wherein a wavelength of the infrared spectroscopy is within a range of frequencies between 400 nanometers and 2500 nanometers.

In Example 6, the subject matter of Examples 1-5 includes, wherein the sample is prepared directly from a mobile tanker or a bulk tanker and wherein the method is performed on-site where the sample is extracted.

In Example 7, the subject matter of Examples 1-6 includes, wherein the spectrometer is a portable spectrometer.

In Example 8, the subject matter of Examples 1-7 includes, wherein outputting the value includes displaying the value on a display of the spectrometer or sending the value to a mobile device for display.

In Example 9, the subject matter of Examples 1-8 includes, wherein the prepared sample is prepared by agitating the sample while melting the sample.

In Example 10, the subject matter of Examples 1-9 includes, wherein outputting the value includes outputting an average or median of two or more iterations of the method.

In Example 11, the subject-matter of Examples 1-10 includes, wherein the sample includes one of an edible tallow sample, an inedible tallow sample, or a tallow sample.

In Example 12, the subject matter of Examples 1-11 includes, wherein the value corresponding to the characteristic for the sample includes a percent of unsaponifiable matter in the sample.

Example 13 is a system for near infrared evaluation of a characteristic of a sample, the system comprising: a spectrometer configured to: emit light comprising a specified range of infrared wavelengths; receive a reflection from a prepared sample of the sample; and establish reflectance data corresponding to the received reflection; and a processor circuit coupled to a memory circuit and communicatively coupled to the spectrometer, the processor circuit configured to: determine a value corresponding to the characteristic for the sample based on a result of the scan; and output the value.

In Example 14, the subject matter of Example 13 includes, wherein the prepared sample is prepared by covering the sample in a petri dish or a slurry cup.

In Example 15, the subject matter of Examples 13-14 includes, wherein the infrared spectroscopy includes infrared transmission spectroscopy or infrared reflection spectroscopy.

In Example 16, the subject matter of Examples 13-15 includes, wherein a wavelength of the infrared spectroscopy is within a near infrared spectrum.

In Example 17, the subject matter of Examples 13-16 includes, wherein a wavelength of the infrared spectroscopy is within a range of frequencies between 400 nanometers and 2500 nanometers.

In Example 18, the subject matter of Examples 13-17 includes, wherein the sample is prepared directly from a mobile tanker or a bulk tanker and wherein the method is performed on-site where the sample is extracted.

In Example 19, the subject matter of Examples 13-18 includes, wherein the spectrometer is a portable spectrometer.

In Example 20, the subject matter of Examples 13-19 includes, wherein the spectrometer includes a display, and wherein to output the value, the processor circuit is configured to cause the display to present the value.

In Example 21, the subject matter of Examples 13-20 includes, wherein the prepared sample is prepared by agitating the sample while melting the sample.

In Example 22, the subject matter of Examples 13-21 includes, wherein to output the value, the processor circuit is configured to determine a second value and output an average of the value and the second value.

In Example 23, the subject matter of Examples 13-22 includes, wherein the sample includes one of an edible tallow sample, an inedible tallow sample, or a tallow sample.

In Example 24, the subject matter of Examples 13-23 includes, wherein the value corresponding to the characteristic for the sample includes a percent of unsaponifiable matter in the sample.

Example 133 is a method for near infrared evaluation of a characteristic of a tallow sample, the method comprising: receiving a prepared sample of the tallow sample at a spectrometer; scanning, using the spectrometer, the prepared sample with infrared spectroscopy; determining, using a processor, a percent of unsaponifiable matter in the tallow sample based on a result of the scan; and outputting the percent of unsaponifiable matter in the tallow sample.

In Example 134, the subject matter of Example 133 includes, wherein the prepared sample is prepared by covering the tallow sample in a petri dish or a slurry cup.

In Example 135, the subject matter of Examples 133-134 includes, wherein the infrared spectroscopy includes infrared transmission spectroscopy or infrared reflection spectroscopy.

In Example 136, the subject matter of Examples 133-135 includes, wherein a wavelength of the infrared spectroscopy is within a near infrared spectrum.

In Example 137, the subject matter of Examples 133-136 includes, wherein a wavelength of the infrared spectroscopy is within a range of frequencies between 400 nanometers and 2500 nanometers.

In Example 138, the subject matter of Examples 133-137 includes, wherein the tallow sample is prepared directly from a mobile tanker or a bulk tanker and wherein the method is performed on-site where the tallow sample is extracted.

In Example 139, the subject matter of Examples 133-138 includes, wherein the spectrometer is a portable spectrometer.

In Example 140, the subject matter of Examples 133-139 includes, wherein outputting the percent of unsaponifiable matter in the tallow sample includes displaying the percent of unsaponifiable matter in the tallow sample on a display of the spectrometer or sending the percent of unsaponifiable matter in the tallow sample to a mobile device for display.

In Example 141, the subject matter of Examples 133-140 includes, wherein the prepared sample is prepared by agitating the tallow sample while melting the tallow sample.

Example 142 is a system for near infrared evaluation of a characteristic of an tallow sample, the system comprising: a spectrometer configured to: emit light comprising a specified range of infrared wavelengths; receive a reflection from a prepared sample of the tallow sample; and establish reflectance data corresponding to the received reflection; and a processor circuit coupled to a memory circuit and communicatively coupled to the spectrometer, the processor circuit configured to: determine a percent of unsaponifiable matter in the tallow sample corresponding to the characteristic for the tallow sample based on a result of the scan; and output the percent of unsaponifiable matter in the tallow sample.

In Example 143, the subject matter of Example 142 includes, wherein the prepared sample is prepared by covering the tallow sample in a petri dish or a slurry cup.

In Example 144, the subject matter of Examples 142-143 includes, wherein the infrared spectroscopy includes infrared transmission spectroscopy or infrared reflection spectroscopy.

In Example 145, the subject matter of Examples 142-144 includes, wherein a wavelength of the infrared spectroscopy is within a near infrared spectrum.

In Example 146, the subject matter of Examples 142-145 includes, wherein a wavelength of the infrared spectroscopy is within a range of frequencies between 400 nanometers and 2500 nanometers.

In Example 147, the subject matter of Examples 142-146 includes, wherein the tallow sample is prepared directly from a mobile tanker or a bulk tanker and wherein the method is performed on-site where the tallow sample is extracted.

In Example 148, the subject matter of Examples 142-147 includes, wherein the spectrometer is a portable spectrometer.

In Example 149, the subject matter of Examples 142-148 includes, wherein the spectrometer includes a display, and wherein to output the percent of unsaponifiable matter in the tallow sample, the processor circuit is configured to cause the display to present the percent of unsaponifiable matter in the tallow sample.

In Example 150, the subject matter of Examples 142-149 includes, wherein the prepared sample is prepared by agitating the tallow sample while melting the tallow sample.

In Example 186, the subject matter of Examples 178-185 includes, wherein outputting the value includes outputting an average or median of two or more iterations of the method.

Example 187 is at least one machine-readable medium including instructions that, when executed by processing circuitry, cause the processing circuitry to perform operations to implement of any of Examples 1-186.

Example 188 is an apparatus comprising means to implement of any of Examples 1-186.

Example 189 is a system to implement of any of Examples 1-186.

Example 190 is a method to implement of any of Examples 1-186.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The claimed invention is:

1. A method for near infrared evaluation of a characteristic of a tallow sample, the method comprising:
   receiving a prepared sample of the tallow sample at a spectrometer;
   scanning, using the spectrometer, the prepared sample with infrared spectroscopy;
   determining, using a processor, a percent of unsaponifiable matter in the tallow sample based on a result of the scan; and
   outputting the percent of unsaponifiable matter in the tallow sample.

2. The method of claim 1, wherein the prepared sample is prepared by covering the tallow sample in a petri dish or a slurry cup.

3. The method of claim 1, wherein the infrared spectroscopy includes infrared transmission spectroscopy or infrared reflection spectroscopy.

4. The method of claim 1, wherein a wavelength of the infrared spectroscopy is within a near infrared spectrum.

5. The method of claim 1, wherein a wavelength of the infrared spectroscopy is within a range of frequencies between 400 nanometers and 2500 nanometers.

6. The method of claim 1, wherein the tallow sample is prepared directly from a mobile tanker or a bulk tanker and wherein the method is performed on-site where the tallow sample is extracted.

7. The method of claim 1, wherein the spectrometer is a portable spectrometer.

8. The method of claim 1, wherein outputting the percent of unsaponifiable matter in the tallow sample includes displaying the percent of unsaponifiable matter in the tallow sample on a display of the spectrometer or sending the percent of unsaponifiable matter in the tallow sample to a mobile device for display.

9. The method of claim 1, wherein the prepared sample is prepared by agitating the tallow sample while melting the tallow sample.

10. A system for near infrared evaluation of a characteristic of a tallow sample, the system comprising:
    a spectrometer configured to:
        emit light comprising a specified range of infrared wavelengths;
        receive a reflection from a prepared sample of the tallow sample; and
        establish reflectance data corresponding to the received reflection; and
    a processor circuit coupled to a memory circuit and communicatively coupled to the spectrometer, the processor circuit configured to:
        determine a percent of unsaponifiable matter in the tallow sample corresponding to the characteristic for the tallow sample based on the reflectance data; and
        output the percent of unsaponifiable matter in the tallow sample.

* * * * *